United States Patent
Giles et al.

(10) Patent No.: US 11,504,132 B2
(45) Date of Patent: Nov. 22, 2022

(54) EMBOLISATION DEVICE FOR PROMOTING BLOOD CLOT FORMATION AND A METHOD OF RETRIEVING THE SAME FROM A BODILY LUMEN

(71) Applicants: Clearstream Technologies Limited, County Wexfod (IE); Ciaran Giles, Enniscorthy (IE); Stephen Sheridan, Enniscorthy (IE)

(72) Inventors: Ciaran Giles, Enniscorthy (IE); Stephen Sheridan, Enniscorthy (IE)

(73) Assignee: CLEARSTREAM TECHNOLOGIES LIMITED, Enniscorthy (IE)

( * ) Notice: Subject to any disclaimer, the term of this patent is extended or adjusted under 35 U.S.C. 154(b) by 0 days.

(21) Appl. No.: 17/279,230

(22) PCT Filed: Jul. 25, 2019

(86) PCT No.: PCT/EP2019/070045
§ 371 (c)(1),
(2) Date: Mar. 24, 2021

(87) PCT Pub. No.: WO2021/013352
PCT Pub. Date: Jan. 28, 2021

(65) Prior Publication Data
US 2021/0307762 A1 Oct. 7, 2021

(51) Int. Cl.
*A61B 17/12* (2006.01)
*A61B 17/00* (2006.01)

(52) U.S. Cl.
CPC .... *A61B 17/12177* (2013.01); *A61B 17/1204* (2013.01); *A61B 17/12109* (2013.01);
(Continued)

(58) Field of Classification Search
CPC ........ A61F 2/01; A61F 2/013; A61B 17/0057; A61B 17/12022; A61B 17/12113;
(Continued)

(56) References Cited

U.S. PATENT DOCUMENTS

| 2005/0274384 A1 | 12/2005 | Tran et al. |
| 2006/0184194 A1* | 8/2006 | Pal .......................... A61F 2/013 |
| | | 606/200 |

(Continued)

FOREIGN PATENT DOCUMENTS

| DE | 102005053434 A1 | 3/2007 |
| WO | 2005074845 A1 | 8/2005 |
| WO | 2013025531 A1 | 2/2013 |

OTHER PUBLICATIONS

International Search Report and Written Opinion pertaining to PCT/EP2019/070045, dated Apr. 17, 2020.
(Continued)

*Primary Examiner* — Katherine M Shi
*Assistant Examiner* — Mikail A Mannan
(74) *Attorney, Agent, or Firm* — Dinsmore & Shohl LLP

(57) ABSTRACT

An embolisation device (10) for promoting clot formation in a bodily lumen (L) and having a collapsed delivery configuration for delivery of the embolisation device (10) into, and retrieval of the embolisation device (10) from, the bodily lumen (L) and an expanded deployed configuration for anchoring the embolisation device (10) in the bodily lumen (L). The embolisation device (10) comprises a tubular cage (20) having a collapsed delivery configuration and an expanded deployed configuration. The embolisation device further comprises an embolisation member (30) disposed in the tubular cage (20), the embolisation member (30) comprising a stem (31) and a plurality of flexible bristles (32) extending outwardly from the stem, the plurality of flexible bristles having a collapsed delivery configuration and an
(Continued)

expanded deployed configuration. The embolisation device (10) is configured such that as the tubular cage (20) is transitioned from its expanded deployed configuration to its collapsed delivery configuration the plurality of flexible bristles (32) is urged by the tubular cage (20) from the expanded deployed configuration of the flexible bristles (32) to the collapsed delivery configuration of the flexible bristles (32).

21 Claims, 8 Drawing Sheets

(52) U.S. Cl.
CPC ............... *A61B 17/12172* (2013.01); *A61B 2017/00867* (2013.01); *A61B 2017/12095* (2013.01)

(58) Field of Classification Search
CPC .......... A61B 17/1214; A61B 17/12145; A61B 17/1215; A61B 17/12163; A61B 17/12109
See application file for complete search history.

(56) References Cited

U.S. PATENT DOCUMENTS

| | | | |
|---|---|---|---|
| 2009/0306702 A1* | 12/2009 | Miloslavski | A61B 17/221 606/200 |
| 2015/0039020 A1* | 2/2015 | Cragg | A61B 17/12172 606/200 |
| 2016/0166257 A1* | 6/2016 | Allen | A61B 17/12113 606/200 |
| 2017/0007260 A1 | 1/2017 | O'Brien et al. | |
| 2019/0110880 A1* | 4/2019 | Fox | A61B 17/12177 |
| 2019/0142435 A1 | 5/2019 | DeMeritt | |

OTHER PUBLICATIONS

International Preliminary Report on Patentability pertaining to PCT/EP2019/070045, dated Oct. 28, 2020.

* cited by examiner

EMBOLISATION DEVICE FOR PROMOTING BLOOD CLOT FORMATION AND A METHOD OF RETRIEVING THE SAME FROM A BODILY LUMEN

CROSS-REFERENCE TO RELATED APPLICATION

This application is a National Stage Entry, under 35 U.S.C. § 371, of International Patent Application No. PCT/EP2019/070045, filed Jul. 25, 2019, the entirety of which is hereby incorporated by reference.

TECHNICAL FIELD

The present disclosure relates to an embolisation device for promoting clot formation in a bodily lumen and having a collapsed delivery configuration for delivery of the embolisation device into, and retrieval of the embolisation device from, the bodily lumen and an expanded deployed configuration for anchoring the embolisation device in the bodily lumen. The present disclosure also relates to a method of retrieving an embolisation device from a bodily lumen of a patient.

BACKGROUND

Embolisation devices may be deployed in the vasculature at a particular location by a medical practitioner so as to promote blood clot formation and ultimately occlude the blood vessel. However, typical embolisation devices may be prone to migration within the vasculature which may cause serious adverse effects.

To reduce migration, some embolisation devices may include a number of bristles or fibres extending radially outwardly from a central stem. The bristles are configured to contact the bodily lumen and anchor the embolisation device in the lumen due to friction between the bristles and the wall of the lumen.

However, in these embolisation devices, the bristles are unconfined. This means that these embolisation devices, once deployed, can only be partially recaptured as once the proximal bristles are deployed, any attempt to recapture and retrieve the device would lead to them becoming reoriented in the wrong direction. This reorientation of the bristles may cause damage to the device itself or the bodily lumen within which it is deployed.

In view of the above, there is a need for an improved embolisation device which is capable of being fully recaptured in a safe and convenient manner. There is also a need for an improved method of fully recapturing an improved embolisation device from the bodily lumen of a patient in a safe and convenient manner.

BRIEF DESCRIPTION OF THE DRAWINGS

To enable better understanding of the present disclosure, and to show how the same may be carried into effect, reference will now be made, by way of example only, to the accompanying drawings, in which.

DETAILED DESCRIPTION

Figure 1:
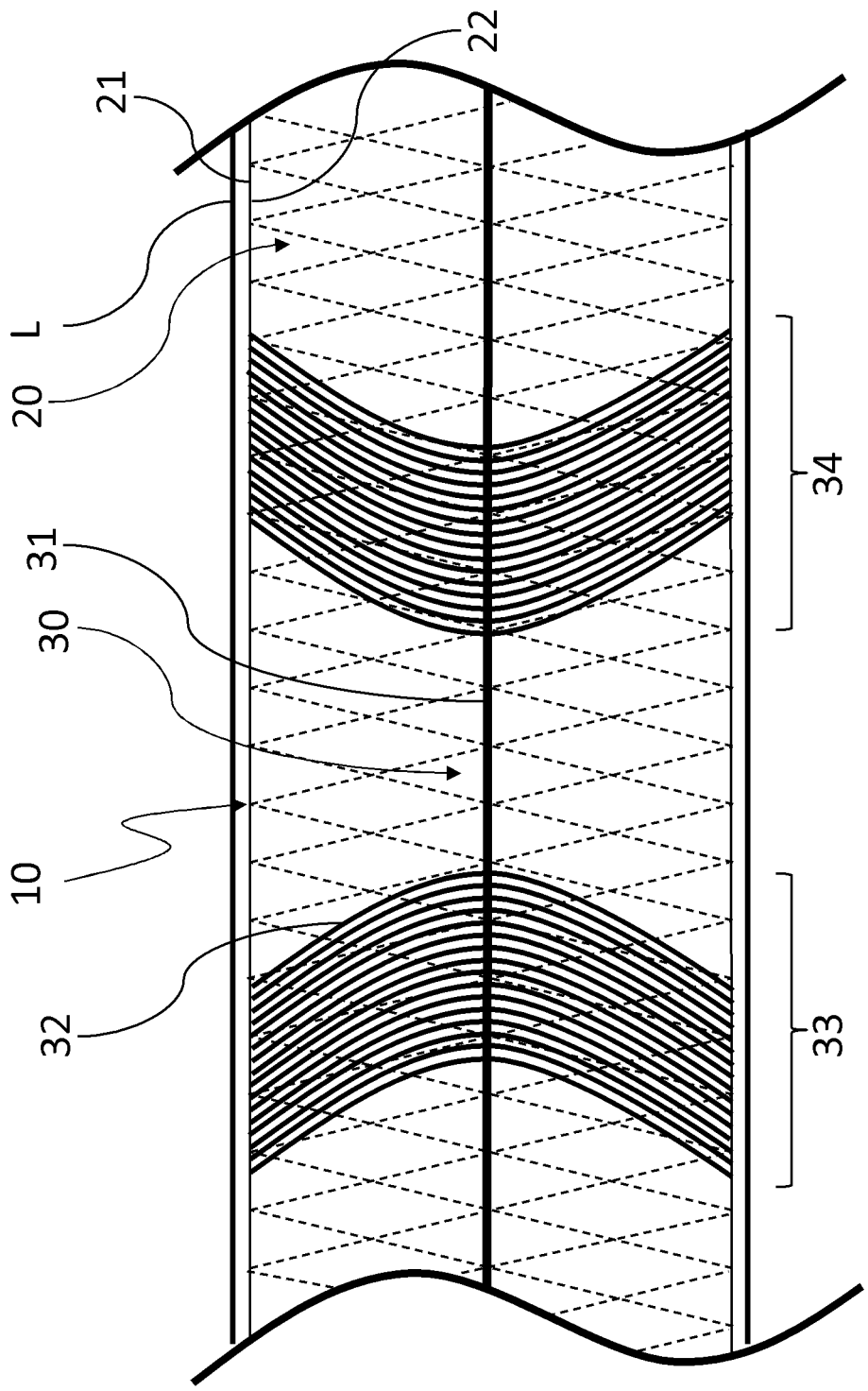
FIG. 1 shows a side view of an embolisation device according to the present disclosure in an expanded deployed configuration.

An embolisation device is a permanent or semi-permanent implantable device which may be received within a bodily lumen so as to promote clot formation therein. Such embolisation devices may have a collapsed delivery configuration and an expanded deployed configuration. The collapsed delivery configuration may be such that the device may be loaded into a delivery device, such as a delivery catheter.

In one aspect of the present disclosure, there is disclosed an embolisation device for promoting blood clot formation in a bodily lumen and having a collapsed delivery configuration for delivery of the embolisation device into, and retrieval of the embolisation device from, the bodily lumen and an expanded deployed configuration for anchoring the embolisation device in the bodily lumen. The embolisation device may comprise a tubular cage having a collapsed delivery configuration and an expanded deployed configuration. The embolisation device may further comprise an embolisation member disposed in the tubular cage, the embolisation member comprising a stem and a plurality of flexible bristles extending outwardly from the stem, the plurality of flexible bristles having a collapsed delivery configuration and an expanded deployed configuration. The embolisation device may be configured such that as the tubular cage is transitioned from its expanded deployed configuration to its collapsed delivery configuration the plurality of flexible bristles is urged by the tubular cage from the expanded deployed configuration of the flexible bristles to the collapsed delivery configuration of the flexible bristles.

In some embodiments this may result in the embolisation device being capable of being fully recaptured from the bodily lumen of a patient in a safe and convenient manner.

Throughout this disclosure the term 'embolisation device' may refer to a device which may be permanently or semi-permanently implanted in a bodily lumen. Accordingly, the 'embolisation device' may be configured to be disposed within the bodily lumen for a period of time, such as a number of days, or disposed in the lumen indefinitely. To this end, the 'embolisation device' may be configured to be selectively detached from a delivery element so that it may be implanted in the bodily lumen in isolation.

Throughout this disclosure the term 'bodily lumen' may refer to the inside space within a tubular structure of the human or animal body. The 'bodily lumen' may be, for example, an artery or vein.

Throughout this disclosure the term 'collapsed delivery configuration' of an element may refer to a configuration of the element which has a smaller radial extent than an 'expanded deployed configuration of the element.

Throughout this disclosure the term 'to anchor' may refer to partly or fully securing an element in a position.

Throughout this disclosure the term 'tubular cage' may refer to a structure of bars, wires, mesh or braid which has been formed into a tube-like shape.

In the expanded deployed configuration of the tubular cage, the tubular cage may be configured to contact the inside of the bodily lumen.

In some embodiments this may result in the tubular cage providing further resistance to migration of the embolisation device.

In the expanded deployed configuration of the embolisation device, the tubular cage and at least some of the plurality of flexible bristles together may anchor the embolisation device in the bodily lumen.

In some embodiments, this may result in the bristles together with the tubular cage providing an increased force against the inside wall of the bodily lumen resulting in increased friction between the embolisation device and the lumen wall and hence an increased resistance to migration of the embolisation device.

In the expanded deployed configuration of the embolisation device a first segment of the plurality of flexible bristles may point in one direction along the longitudinal axis of the tubular cage. In the collapsed delivery configuration of the embolisation device the first segment of the plurality of flexible bristles may point in the same direction.

In some embodiments this may result in an embolisation device where the bristles do not reorient themselves when the embolisation device is urged into the collapsed delivery configuration to more safely and conveniently recapture the embolisation device from a bodily lumen of a patient.

In the expanded deployed configuration of the embolisation device a second segment of the plurality of flexible bristles may point in a direction opposite to the direction of the first segment of flexible bristles. In the collapsed delivery configuration of the embolisation device the second segment of the plurality of flexible bristles may point in the same opposite direction.

In some embodiments having segments of bristles pointing in opposite directions may result in having an increased resistance to migration in both directions.

The tubular cage may be self-expanding.

In some embodiments this may result in a device which is easy, quick and convenient to deploy. In some embodiments this may further result in the tubular cage exerting an increased force against the inside wall of the bodily lumen resulting in increased resistance to migration of the embolisation device.

The tubular cage may be made from a shape-memory alloy.

The tubular cage may be made from Nitinol.

The stem may be disposed substantially parallel to the longitudinal axis of the tubular cage.

The tubular cage may have hooks which are configured to anchor the embolisation device in the bodily lumen.

In some embodiments, this may result in increased resistance to migration.

The hooks may be disposed on the outside surface of the tubular cage.

The hooks may be made from Nitinol.

A set of the hooks may point in a generally uniform direction along the longitudinal axis of the tubular cage.

A first set and a second set of the hooks may point in respective directions along the longitudinal axis of the tubular cage that are generally opposite from each other.

In some embodiments, this may result in increased resistance to migration in both directions.

At least some of the flexible bristles may be attached to the inside surface of the tubular cage.

In some embodiments, this may result in an improved collapsed delivery configuration of the flexible bristles and therefore more convenient recapture of the embolisation device from a bodily lumen.

The embolisation member may further comprise a membrane configured to restrict flow through the bodily lumen.

In some embodiments, this may result in quicker blood clot formation and improved embolisation when the embolisation device is disposed in the bodily lumen.

The membrane may be conical or cup-shaped.

In some embodiments, this may allow the membrane to be more easily collapsed into a collapsed delivery configuration.

The embolisation member may further comprise a connector at the proximal end of the stem for connecting the stem to a guidewire.

In some embodiments this may allow a guidewire to be easily attached to the embolisation device and a catheter to be slid over the tubular cage to urge the embolisation device into a collapsed delivery configuration for recapture and retrieval.

The connector may be a threaded connector.

In some embodiments, this may allow the guidewire to be easily attached to the embolisation device by rotating it.

The connector may be one of a hooked connector, a ball and claw grasping connector or a slot detachment mechanism connector.

A proximal end of the tubular cage may be tapered.

In some embodiments, this may allow a catheter to conveniently slide over the outer surface of the tubular cage to urge the embolisation device into a collapsed delivery configuration for retrieval.

The proximal end of the tubular cage may be attached to the stem of the embolisation member.

In some embodiments, this may allow the embolisation device to be more easily collapsed into the collapsed delivery configuration for recapture of the embolisation device.

In a second aspect of the present disclosure, there is disclosed a method of retrieving an embolisation device from a bodily lumen of a patient. The embolisation device may comprise a tubular cage and an embolisation member, wherein the embolisation member comprises a stem and a plurality of flexible bristles extending outwardly from the stem. The method may comprise collapsing the tubular cage from an expanded deployed configuration into a collapsed delivery configuration inside the bodily lumen, wherein as the tubular cage is transitioned from its expanded deployed configuration to its collapsed delivery configuration the plurality of flexible bristles is urged by the tubular cage from the expanded deployed configuration of the flexible bristles to the collapsed delivery configuration of the flexible bristles. The method may further comprise removing the embolisation device from the bodily lumen.

In some implementations, this may result in a method which allows the full recapture of the embolisation device in a convenient and safe manner.

Collapsing the tubular cage may further comprise connecting a guidewire to the proximal end of the embolisation device and sliding a catheter over the tubular cage.

FIG. 1 shows a side view of an embolisation device 10 in an expanded deployed configuration inside a bodily lumen L. The bodily lumen L may be a vein or artery, for example. The embolisation device 10 comprises a tubular cage 20 and an embolisation member 30 disposed inside the tubular cage 20.

The tubular cage 20 is a self-expanding stent cage which may be made from a shape-memory material such a Nitinol. The tubular cage 20 has an expanded deployed configuration, shown in FIG. 1, and a collapsed delivery configuration (see FIG. 2 below) and comprises an outside surface 21 and an inside surface 22. In the expanded deployed configuration, the outside surface 21 of the tubular cage 20 is in contact with the bodily lumen L. FIG. 1 does not show this contact, but rather shows a gap between the outside surface 21 of the tubular cage 20 and the inside wall of the bodily lumen L for clarity and illustrative purposes. In the expanded deployed configuration, the tubular cage 20 may have a diameter of 1.5 mm to 20 mm.

Due to the self-expanding properties of the tubular cage 20, the outside surface 21 will exert a force on the inside wall of the bodily lumen L. The friction between the inside wall of the bodily lumen L and the outside surface 21 will anchor the embolisation device 10 inside the bodily lumen L, to resist migration of the embolisation device 10.

The embolisation member 30 comprises a stem 31 and a plurality of flexible bristles 32. The flexible bristles 32 may be made from Nitinol, Elgiloy or stainless steel or any other shape-memory metal or polymer. The diameter of an individual flexible bristle 32 may range from 0.036 mm (0.0014 inches) to 0.053 mm (0.0021 inches). For example, the diameter of an individual flexible bristle 32 may be 0.381 mm (0.015 inches), 0.445 mm (0.0175 inches) or 0.508 mm (0.02 inches). The stem 31 is disposed substantially parallel to the longitudinal axis of the tubular cage 20. The flexible bristles 32 extend radially outwardly from the stem 31. The overall radial diameter of the expanded flexible bristles 32 may range from 5 mm to 30 mm. The ends of the flexible bristles 32 are attached to the inside surface 22 of the tubular cage 20. A variety of adhesion techniques may be used such as, for example, biocompatible adhesives or welding techniques.

Similarly to the tubular cage 20, the flexible bristles 32 also have an expanded deployed configuration, as shown in FIG. 1, and a collapsed delivery configuration (see FIG. 2 below). The expanded deployed configuration of the flexible bristles 32 and the tubular cage 20 corresponds to the expanded deployed configuration of the overall embolisation device 10. Similarly, the collapsed delivery configuration of the flexible bristles 32 and the tubular cage 20 corresponds to the collapsed delivery configuration of the overall embolisation device 10.

In the expanded deployed configuration, the flexible bristles 32 are biased against the inside surface 21 of the tubular cage 20 so as to exert a force on the inside surface of the tubular cage 20. This results in an increased force exerted by the outside surface 22 of the tubular cage 20 on the inside wall of the bodily lumen L and therefore an increased friction between the outside surface 22 and the inside wall of the bodily lumen L. The tubular cage 20 and the plurality of flexible bristles 32 together therefore anchor the embolisation device 10 in the bodily lumen L.

The flexible bristles 32 and the self-expanding tubular cage 20 combine to exert a greater force on the inside wall of the bodily lumen L than the tubular cage 20 or the embolisation member 30 would on their own. The embolisation device 10 thus has an increased resistance to migration.

Furthermore, when the embolisation device 10 is deployed, the self-expanding tubular cage 20 does not resist the expansion of the flexible bristles 32 but rather helps them expand from their collapsed delivery configuration to their expanded deployed configuration. This results in a faster deployment of the embolisation device 10.

The flexible bristles 32 are grouped into a first segment 33 and a second segment 34, shown in FIG. 1. The flexible bristles 32 of the first segment 33 point in a distal direction and the flexible bristles 32 of the second segment 34 point in a proximal direction. Having different segments of the flexible bristles 32 point in opposite directions, allows the embolisation device 10 to have an increased resistance to migration in both directions. Depending on the required length of the embolisation device 10, the required resistance to migration and the required embolisation timeframe, the embolisation device 10 may comprise any number of bristle segments.

In the expanded deployed configuration, the embolisation device 10 is anchored in the bodily lumen L and is suitable for promoting blood clot formation in the bodily lumen L. The flexible bristles 32 restrict the flow of blood through the lumen L causing an embolus of blood to form and grow to eventually occlude the bodily lumen L.

Figure 2:
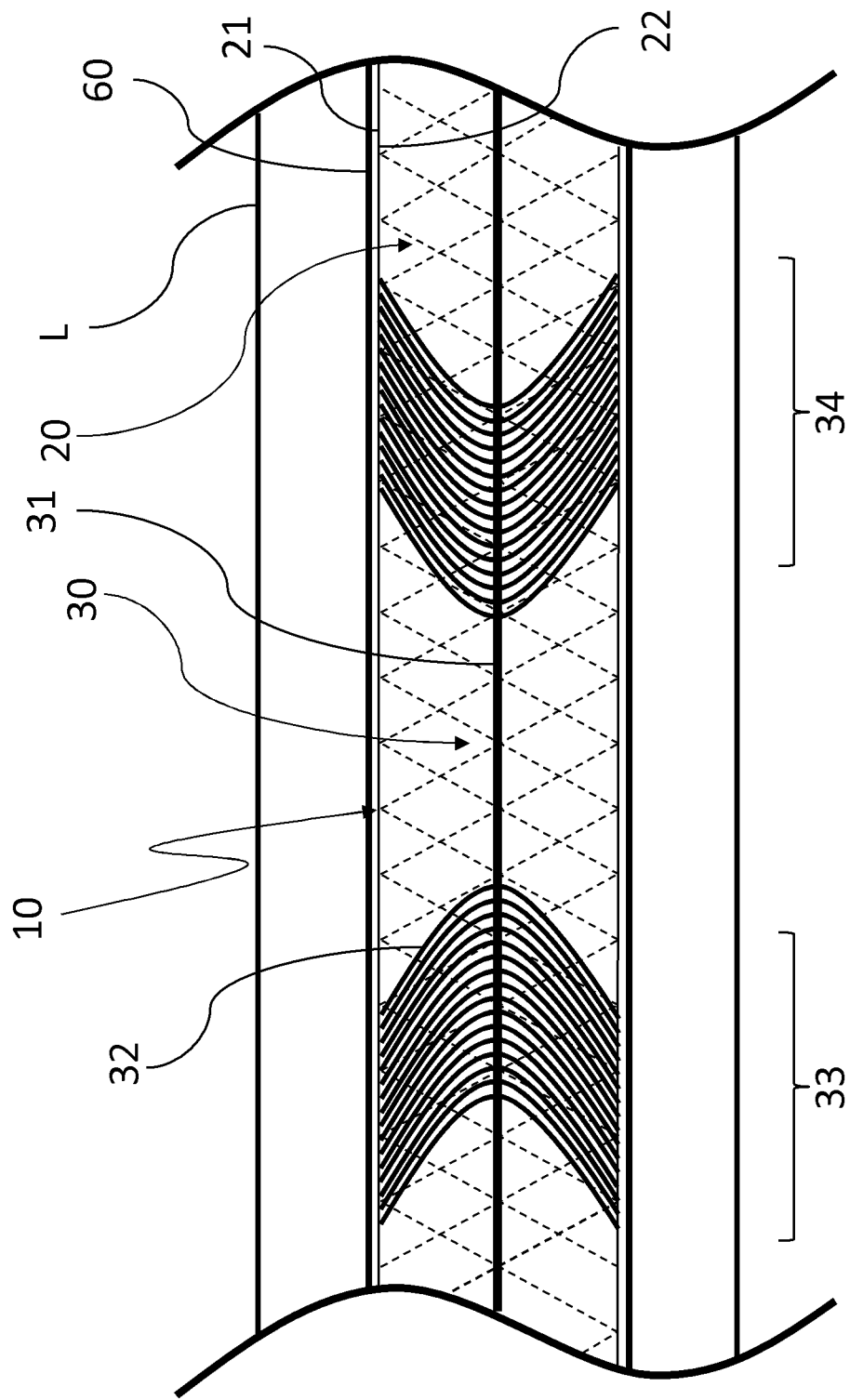
FIG. 2 shows a side view of the embolisation device of FIG. 1 in a collapsed delivery configuration.

FIG. 2 shows a side view of the embolisation device 10 in a collapsed delivery configuration disposed inside a catheter 60. In the collapsed delivery configuration the radial extent of the embolisation device 10 is smaller than in the expanded deployed configuration, shown in FIG. 1.

The flexible bristles 32 and the tubular cage 20 are also in their collapsed delivery configuration, where their radial extent is smaller than in the expanded deployed configuration.

The collapsed delivery configuration is suitable for delivering the embolisation device 10 into the bodily lumen L or retrieving the embolisation device 10 from the bodily lumen L. The radial extent of the embolisation device 10 is small enough so that it can fit inside the lumen of a catheter 60 to deliver it to a desired site in the bodily lumen L or retrieve it from a bodily lumen L.

In the collapsed delivery configuration of FIG. 2, the first segment 33 of the flexible bristles 32 still points in a distal direction and the second segment 34 of the flexible bristles 32 still points in a proximal direction. The orientation of the flexible bristles 32 does not change when the embolisation device 10 is transitioned from the expanded deployed configuration to the collapsed delivery configuration and vice versa. This allows the embolisation device 10 to be collapsed into its collapsed delivery configuration without reorienting the flexible bristles 32 and therefore allows a full recapture and retrieval of the embolisation device 10 from a bodily lumen L in a safe and convenient manner.

FIGS. 3A-3D illustrate a method of fully recapturing the embolisation device 10 and retrieving it from a bodily lumen L using a guidewire 50 and a catheter 60. This method is usually carried out by a physician under fluoroscopy so that the devices and instruments inside the bodily lumen L can be visualized.

Figure 3A:
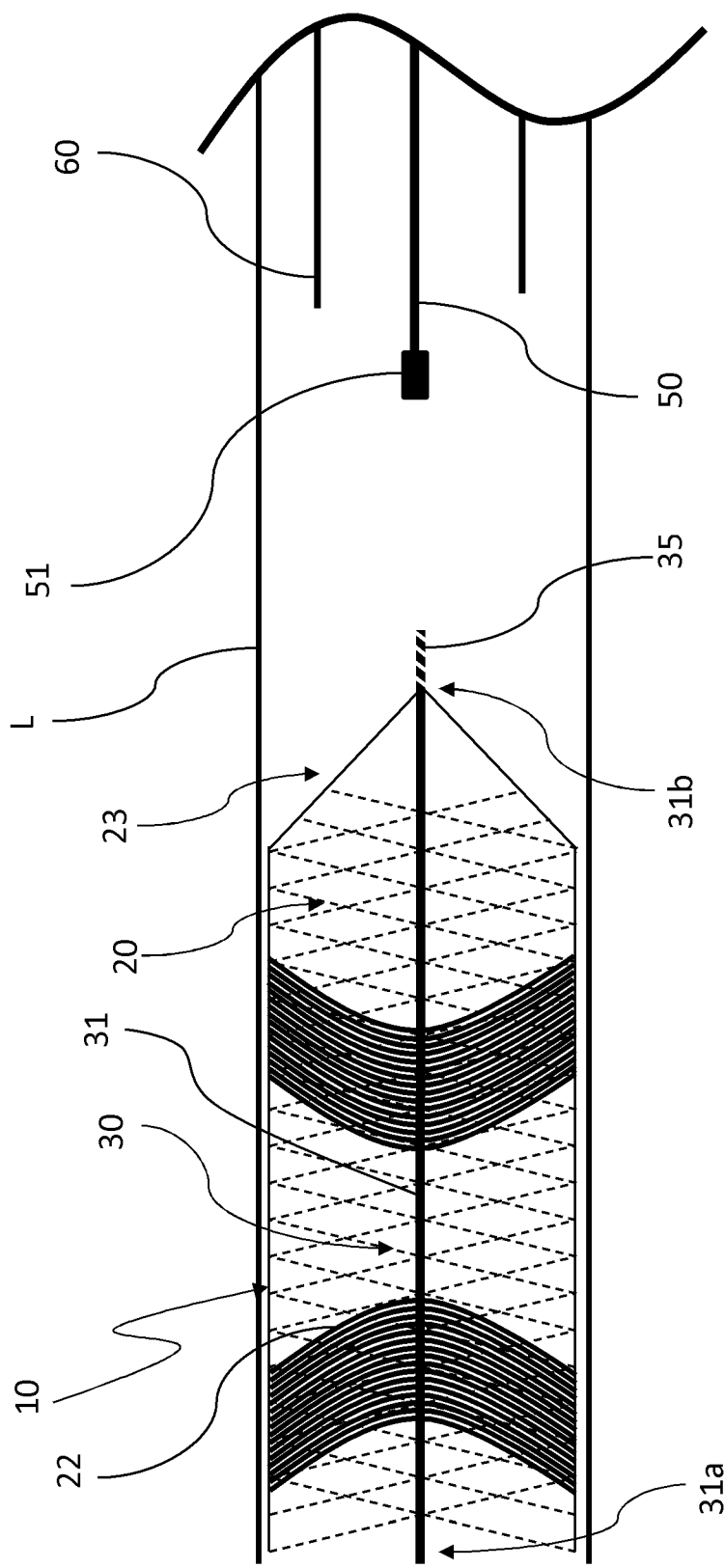
FIG. 3A shows the embolisation device of FIG. 1 in an expanded deployed configuration disposed inside a bodily lumen.

FIG. 3A shows the embolisation device 10 of FIG. 1 in an expanded deployed configuration inside the bodily lumen L.

The stem 31 of the embolisation member 30 has a distal end 31a and a proximal end 31b. The proximal end 31b comprises a male threaded connector 35. The tubular cage 20 has a proximal end 23 which is tapered and attached to the proximal end 31b of the stem 31. For example, the proximal end 23 of the tubular cage 20 may comprise tethers which may be attached to the stem by welding, heat shrinking or through a crimped marker band, for example.

In order to recapture and retrieve the embolisation device 10 from the bodily lumen L, a guidewire 50 and a catheter 60 are introduced into a bodily lumen L of a patient through an access site of the patient's body and advanced to the position where the embolisation device 10 is disposed in the bodily lumen L. The guidewire 50 comprises a female threaded connector 51 at its distal end.

Figure 3B:
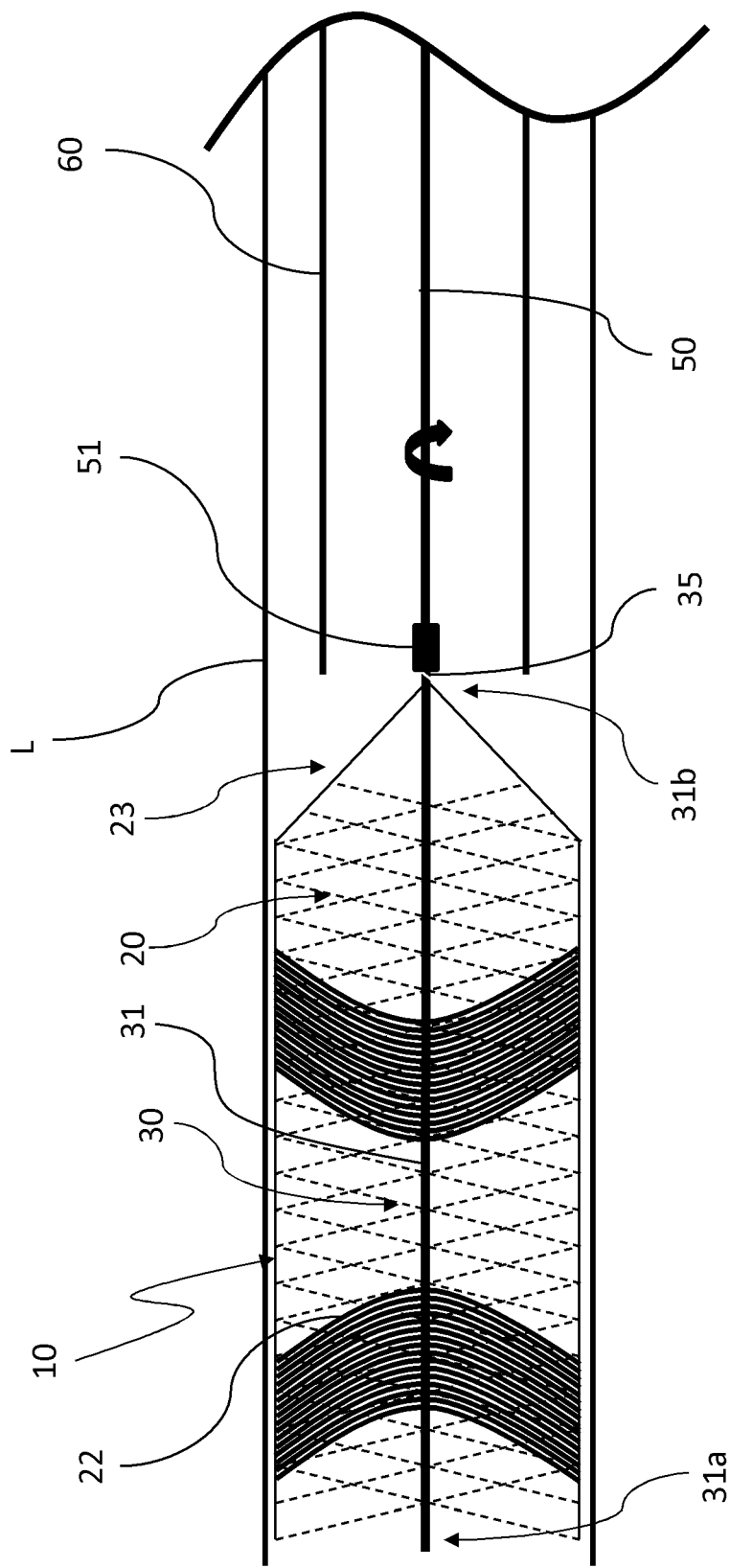
FIG. 3B shows the embolisation device of FIG. 1 in an expanded deployed configuration disposed inside a bodily lumen and connected to a guidewire.

FIG. 3B shows the female threaded connector 51 at the distal end of the guidewire 50 connected to the male threaded connector 35 at the proximal end 31b of the stem 31.

After introducing the guidewire 50 into the bodily lumen L, the guidewire 50 is advanced in a distal direction until the female threaded connector 51 is in contact with the male threaded connector 35. The guidewire 50 is then connected to the stem 31 of the embolisation device 10 by rotating the guidewire 50, so as to connect the female threaded connector 51 of the male threaded connector 35.

Once the guidewire 50 is connected to the embolisation device 10, the catheter 60 is moved in a distal direction towards the embolisation device 10.

Figure 3C:
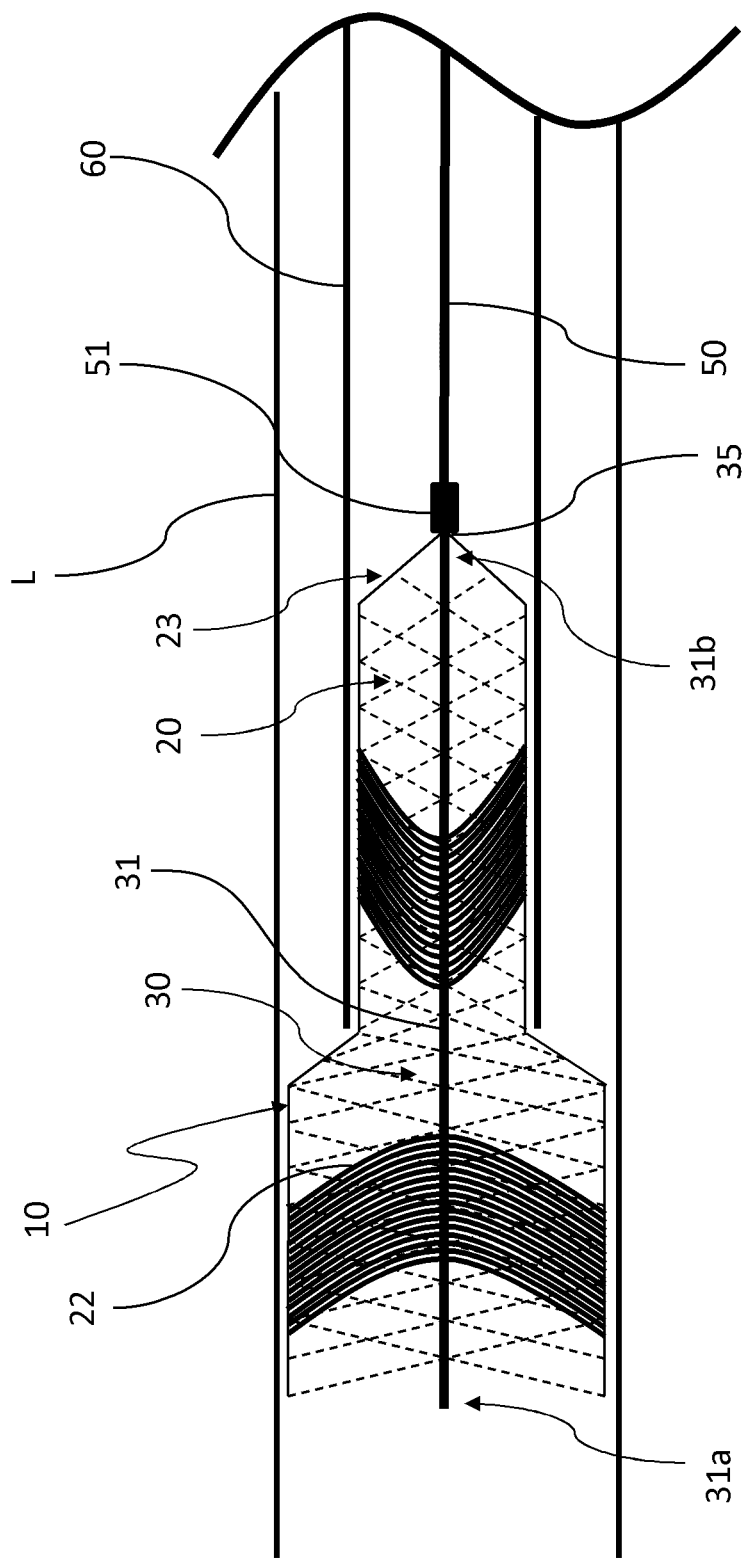
FIG. 3C shows the embolisation device of FIG. 1 disposed inside a bodily lumen being collapsed from an expanded deployed configuration into a collapsed delivery configuration by sliding a catheter over the embolisation device.

FIG. 3C shows half of the length of the embolisation device 10 in the collapsed delivery configuration and the other half in the expanded deployed configuration.

To fully recapture the embolisation device 10, the catheter 60 is slid over the proximal end 23 of the tubular cage 20 and advanced in a distal direction, whilst the embolisation device 10 is secured and held in place by the guidewire 50. The proximal end 23 of the tubular cage 20 is tapered and attached to the stem 31 of the embolisation member 30. This allows the catheter to easily slide over the top of the tubular cage 20 so as to transition the tubular cage 20 from the expanded deployed configuration to the collapsed delivery configuration.

As the tubular cage 20 is transitioned from the expanded deployed configuration into the collapsed delivery configuration of the tubular cage 20 it urges the flexible bristles 32 from the expanded deployed configuration into the collapsed delivery configuration of the flexible bristles 32.

The orientation of the flexible bristles 32 does not change when they are urged from their expanded deployed configuration into their collapsed delivery configuration.

Figure 3D:
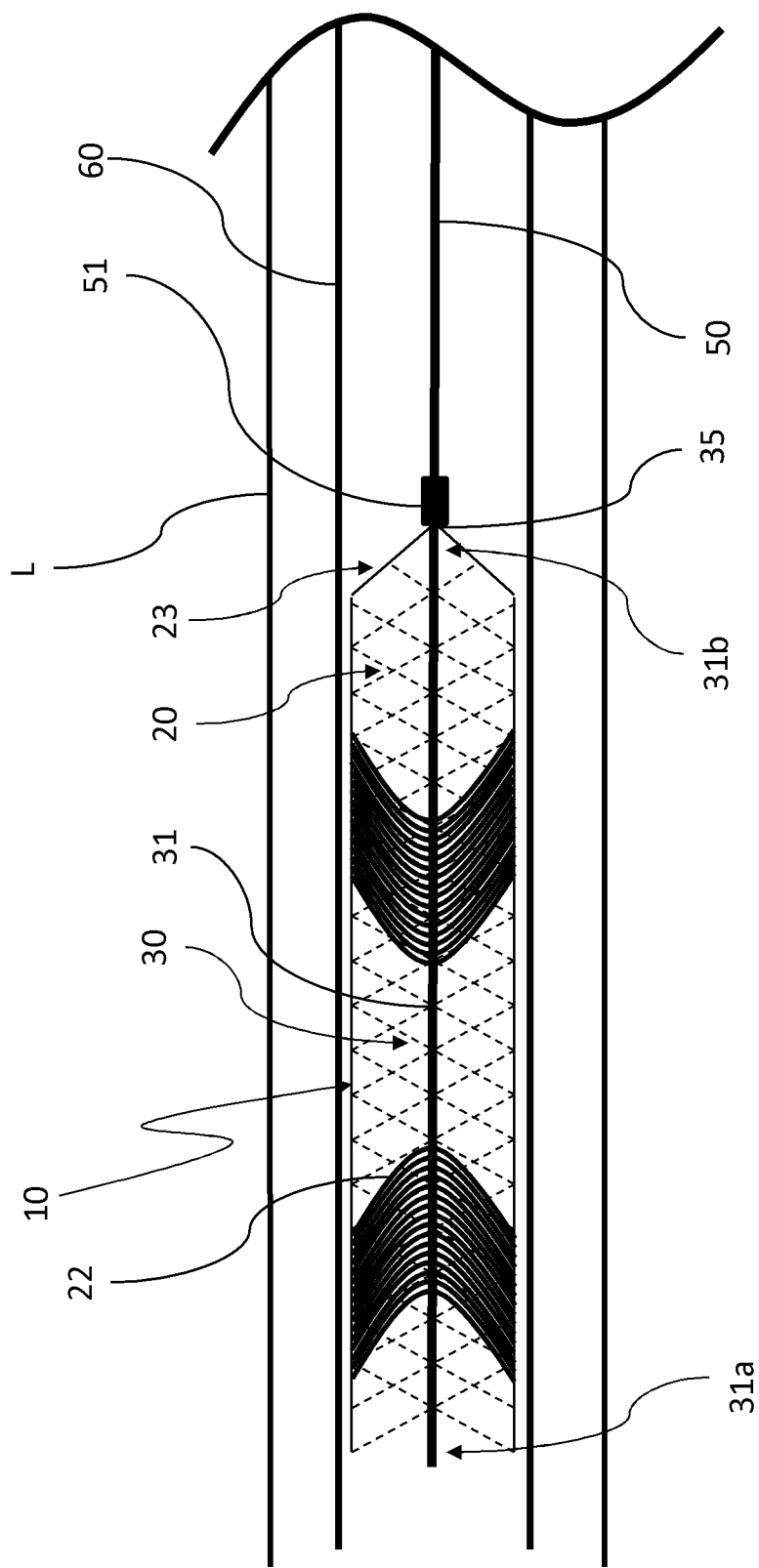
FIG. 3D shows the embolisation device of FIG. 1 in a collapsed delivery configuration inside a catheter inside a bodily lumen.

FIG. 3D shows the embolisation device 10 in a collapsed deployed configuration inside the catheter 60. The catheter 60 has advanced past the proximal end 31a of the stem 31 and the full length of the embolisation device 10 is in a collapsed delivery configuration.

The embolisation device 10 has been fully recaptured in a safe and convenient manner without reorienting the orientation of the flexible bristles 32 or causing any damage to the inside of the bodily lumen L.

The embolisation device 10 may now be retrieved from the body of the patient by pulling the guidewire 50 and the catheter 60 in a proximal direction towards the access site and out of the body of the patient through the access site.

Figure 4:
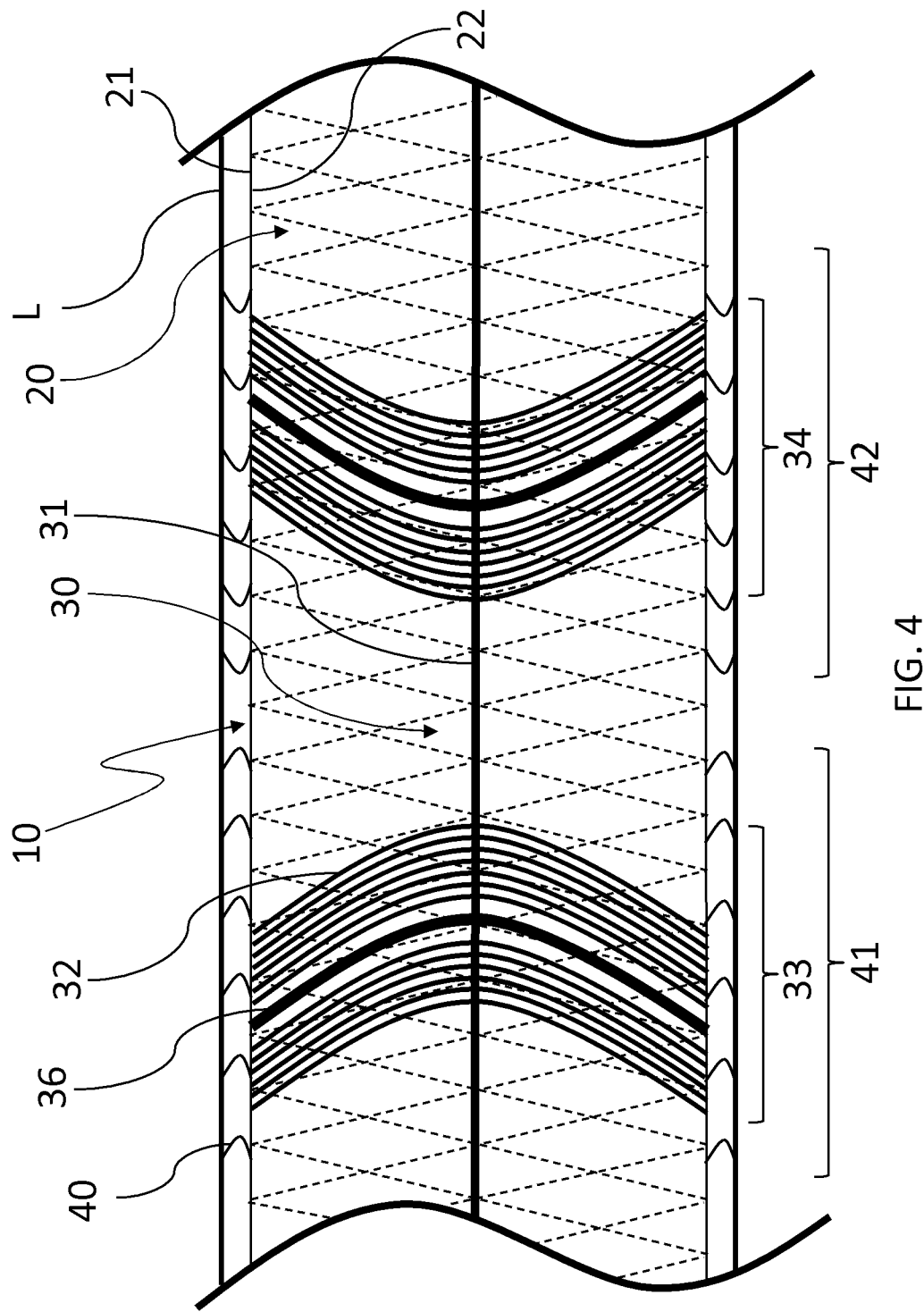
FIG. 4 shows a side view of another embodiment of the embolisation device in an expanded deployed configuration comprising a membrane and hooks disposed on the outside surface of the tubular cage.

FIG. 4 shows another embodiment of embolisation device 10 in an expanded deployed configuration disposed inside a bodily lumen L.

The embolisation device 10 shown in FIG. 4 further comprises hooks 40 disposed on the outside surface 21 of the tubular cage 20. The hooks 40 can be formed from Nitinol which would allow the hooks 40 to be easily bonded to the tubular cage 20.

The hooks 40 are placed all the way along the length of the tubular cage 20. In the expanded deployed configuration of the embolisation device 10, the hooks 40 anchor the embolisation device in the bodily lumen L. The hooks 40 increase the friction between the embolisation device 10 and the inside wall of the bodily lumen L and so provide an increased resistance to migration of the embolisation device 10 when it is deployed in the bodily lumen L.

A first set of hooks 41 points in a distal direction and a second set of hooks 42 points in a proximal direction. Having a first and second set of hooks 40 pointing in opposite directions provides an increased resistance to migration in both directions.

Embolisation device 10 further comprises a membrane 36 disposed inside the first segment 33 of flexible bristles 32, in between the flexible bristles 32. The membrane 36 extends radially outwardly from the stem 31. In the expanded deployed configuration of the embolisation device 10, the membrane 36 restricts the flow of blood through the bodily lumen resulting in quicker blood clot formation and embolisation. The membrane 36 is disc-shaped and has a radial extent equal to the radial extent of the flexible bristles 32. The second segment 34 of flexible bristles 32 also comprises a membrane similar to membrane 36 but pointing in the opposite direction. The membrane 36 may be made from thin film Nitinol, thin film PTFE, a thin film elastomer such as polyurethane or any other type of suitable biocompatible material. The membrane 36 may have a thickness of 4 µm to 35 µm and a radial diameter of 5 mm to 20 mm. For example, the diameter of the membrane 36 may be 6.5 mm, 9 mm or 16 mm. Furthermore, the membrane 36 may be non-permeable or semi-permeable.

The membrane 36 is attached to the inside surface 22 of the tubular cage 20. During deployment of the embolisation device 10, the self-expanding tubular cage 20 will expand into its expanded deployed configuration and help to pull open the membrane 36 to allow for occlusion of the lumen L.

Figure 5:
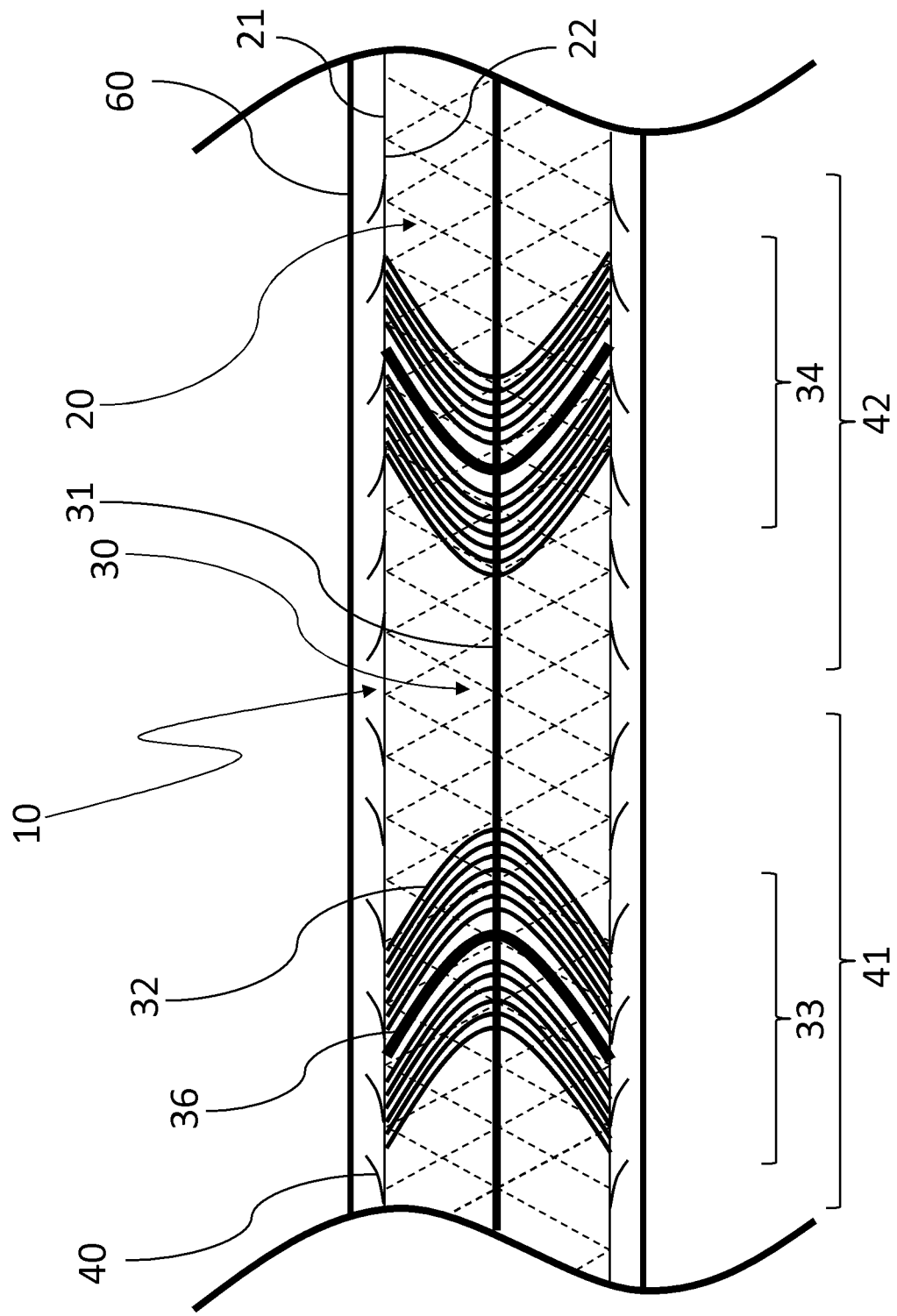
FIG. 5 shows a side view of the embolisation device of FIG. 4 in a collapsed delivery configuration.

FIG. 5 shows the embolisation device 10 of FIG. 4 in a collapsed delivery configuration disposed inside a catheter 60.

The hooks 40 are straightened when the embolisation device 10 is disposed inside the catheter 60 in the collapsed delivery configuration. When the embolisation device 10 is deployed in a bodily lumen L, the hooks will reform into their natural hooked shape, as shown in FIG. 4.

In the collapsed delivery configuration of the embolisation device 10, the membrane 36 will collapse together with the tubular cage 20 and the flexible bristles 32 to form a more compact shape with a smaller radial extent, so as to allow the embolisation device to be disposed inside the lumen of a catheter 60. Similarly to the flexible bristles 32, the orientation of the membrane also does not change when the embolisation device 10 is transitioned from the expanded deployed configuration to the collapsed delivery configuration.

The method illustrated in FIGS. 3A-3D may similarly be carried out with the embolisation device 10 shown in FIGS. 4 and 5.

Various modifications will be apparent to those skilled in the art. For example, the tubular cage 20 does not have to be self-expanding. The tubular cage 20 also does not have to be stent cage but can be formed of any kind of meshed, braided, wire or bar structure.

The flexible bristles 32 do not have to be grouped into segments but can be disposed uniformly along the length of the stem 31. Furthermore, the embolisation device 10 may comprise any number of required segments of flexible bristles 32 and the segments may point in a uniform direction along the longitudinal length of the embolisation device 10 or, alternatively, individual segments may point in opposite directions along the longitudinal length of the embolisation device 10.

Not all of the flexible bristles 32 may be attached to the inside surface 22 of the tubular cage 20. In some embodiments, none of the flexible bristles may be attached to the inside surface of the 22 of the tubular cage 20.

All of the flexible bristles 32 may be the same length or in some embodiments, some of the flexible bristles 32 may be of shorter length than the others.

The proximal end 23 of the tubular cage 20 may not be tapered and may not be attached to the stem 31 of the embolisation device.

The connector at the proximal end 31b of the stem 31 may be a hooked connector, a ball and claw grasping connector, a slot detachment mechanism connector or any other type of suitable connector.

The hooks 40 may all point in a uniform direction along the longitudinal length of the embolisation device 10. This may be a proximal or a distal direction. This would give an increased resistance to migration in one direction. Alternatively, the hooks 40 may be grouped into any number of sets where adjacent sets of hooks 40 point in opposite directions along a longitudinal length of the embolisation device 10.

The hooks 40 may be disposed only along one or several parts of the length of the outside surface 21 of the embolisation device 10.

The membrane 36 may be disposed within a segment of the flexible bristles 32 or it may be disposed between different segments of the flexible bristles 32. Each segment of the flexible bristles may comprise more than one membrane 36 and some segments of the flexible bristles 32 may not comprise a membrane 36 at all.

The membrane 36 may have a smaller radial extent than the flexible bristles 32. Furthermore, the membrane 36 may not be attached to the inside surface 22 of the tubular cage 20.

The membrane 36 may not be disc-shaped but may have a conical or cup-like shape.

The membrane 36 may further be disposed substantially perpendicular to the longitudinal axis of the tubular cage 20.

Table 1 below contains preferable dimensions for the implant.

TABLE 1

| Membrane thickness | Membrane Diameter | Tubular Cage Diameter | Bristle Diameter |
|---|---|---|---|
| 4-35 microns | 6.5 mm | 1.5-4 mm | 0.381 mm (0.015") |
| 4-35 microns | 9 mm | 4 mm-11 mm | 0.445 mm (0.0175") |
| 4-35 microns | 16 mm | 11 mm-20 mm | 0.508 mm (0.02") |

All of the above are fully within the scope of the present disclosure, and are considered to form the basis for alternative embodiments in which one or more combinations of the above described features are applied, without limitation to the specific combination disclosed above.

In light of this, there will be many alternatives which implement the teaching of the present disclosure. It is expected that one skilled in the art will be able to modify and adapt the above disclosure to suit its own circumstances and requirements within the scope of the present disclosure, while retaining some or all technical effects of the same, either disclosed or derivable from the above, in light of his common general knowledge in this art. All such equivalents, modifications or adaptations fall within the scope of the present disclosure.

The invention claimed is:

1. An embolisation device for promoting clot formation in a bodily lumen and having a collapsed delivery configuration for delivery of the embolisation device into, and retrieval of the embolisation device from, the bodily lumen and an expanded deployed configuration for anchoring the embolisation device in the bodily lumen, the embolisation device comprising:
a tubular cage having a collapsed delivery configuration and an expanded deployed configuration; and
an embolisation member disposed in the tubular cage, the embolisation member comprising a stem and a plurality of flexible bristles extending outwardly from the stem, the plurality of flexible bristles having a collapsed delivery configuration and an expanded deployed configuration configured to promote clot formation and occlude the bodily lumen,
wherein the embolisation device is configured such that as the tubular cage is transitioned from its expanded deployed configuration to its collapsed delivery configuration the plurality of flexible bristles is urged by the tubular cage from the expanded deployed configuration of the flexible bristles to the collapsed delivery configuration of the flexible bristles,
wherein in the expanded deployed configuration of the embolisation device a first segment of the plurality of flexible bristles points in one direction along the longitudinal axis of the tubular cage, and wherein in the collapsed delivery configuration of the embolisation device the first segment of the plurality of flexible bristles points in the same direction.

2. The embolisation device of claim 1, wherein, in the expanded deployed configuration of the tubular cage, the tubular cage is configured to contact the inside of the bodily lumen.

3. The embolisation device of claim 1, wherein, in the expanded deployed configuration of the embolisation device, the tubular cage and at least some of the plurality of flexible bristles together anchor the embolisation device in the bodily lumen.

4. The embolisation device of claim 1, wherein, in the expanded deployed configuration of the embolisation device a second segment of the plurality of flexible bristles points in a direction opposite to the direction of the first set of flexible bristles, and wherein in the collapsed delivery configuration of the embolisation device the second segment of the plurality of flexible bristles points in the same opposite direction.

5. The embolisation device of claim 1, wherein the tubular cage is self-expanding.

6. The embolisation device of claim 1, wherein the tubular cage is made from a shape memory alloy.

7. The embolisation device of claim 1, wherein the tubular cage is made from Nitinol.

8. The embolisation device of claim 1, wherein the stem is disposed substantially parallel to the longitudinal axis of the tubular cage.

9. The embolisation device of claim 1, wherein the tubular cage has hooks which are configured to anchor the embolisation device in the bodily lumen.

10. The embolisation device of claim 9, wherein the hooks are disposed on the outside surface of the tubular cage.

11. The embolisation device of claim 9, wherein the hooks are made from Nitinol.

12. The embolisation device of claim 9, wherein a set of the hooks point in a generally uniform direction along the longitudinal axis of the tubular cage.

13. The embolisation device of claim 9, wherein a first set and a second set of the hooks point in respective directions along the longitudinal axis of the tubular cage that are generally opposite from each other.

14. The embolisation device of claim 1, wherein each of the plurality of flexible bristles comprises a first end and a second end, each of the plurality of flexible bristles is attached to the stem at the first end, and each of the flexible bristles are attached to an inside surface of the tubular cage at the second end.

15. The embolisation device of claim 1, wherein the embolisation member further comprises a membrane configured to restrict flow through the bodily lumen.

16. The embolisation device of claim 15, wherein the membrane is conical or cup-shaped.

17. The embolisation device of claim 1, wherein the embolisation member further comprises a connector at the proximal end of the stem for connecting the stem to a guidewire.

18. The embolisation device of claim 17, wherein the connector is a threaded connector.

19. The embolisation device of claim 17, wherein the connector is one of a hooked connector, a ball and claw grasping connector or a slot detachment mechanism connector.

20. The embolisation device of claim 1, wherein a proximal end of the tubular cage is tapered.

21. The embolisation device of claim 1, wherein the proximal end of the tubular cage is attached to the stem of the embolisation member.

* * * * *